United States Patent [19]

Diehr et al.

[11] Patent Number: 4,659,364
[45] Date of Patent: Apr. 21, 1987

[54] 1-(2-OXYAMINOSULPHONYLPHENYLSULPHONYL)-3-HETEROARYL-ISO-(THIO)-UREAS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochim Riebel, Wuppertal; Wolfgang Roy, Langenfeld; Hans-Joachim Santel; Robert R. Schmidt, both of Cologne, all of Fed. Rep. of Germany

[73] Assignee: Bayer Aktiengesellschaft, Leverkusen, Fed. Rep. of Germany

[21] Appl. No.: 769,192

[22] Filed: Aug. 23, 1985

[30] Foreign Application Priority Data

Aug. 30, 1984 [DE] Fed. Rep. of Germany ....... 3431930

[51] Int. Cl.$^4$ .................... C07D 239/69; A01N 43/54
[52] U.S. Cl. ........................................ 71/92; 544/323; 544/321; 544/332
[58] Field of Search ...................... 544/321, 332, 323; 71/92

[56] References Cited

FOREIGN PATENT DOCUMENTS 117014 8/1984 European Pat. Off. .

Primary Examiner—John M. Ford
Attorney, Agent, or Firm—Sprung Horn Kramer & Woods

[57] ABSTRACT

Herbicidally active novel 1-(2-oxyaminosulphonylphenylsulphonyl)-3-heteroaryl-iso (thio)-ureas of the formula

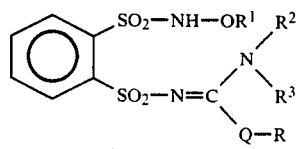

in which
R is optionally substituted alkyl, alkenyl, alkinyl, cycloalkyl-alkyl, cycloalkyl, aralkyl, aryl or heteryl,
$R^1$ is optionally substituted alkyl, alkenyl, alkinyl, cycloalkyl, cycloalkyl-alkyl, aralkyl or aryl,
$R^2$ is hydrogen, or optionally substituted alkyl, alkenyl, alkinyl or aralkyl,
$R^3$ is an optionally substituted and/or optionally fused 6-membered aromatic heterocycle which contains at least one nitrogen atom, and
Q is oxygen or sulphur,
or strong acid-adducts thereof.

8 Claims, No Drawings

1-(2-OXYAMINOSULPHONYLPHENYLSULPHONYL)-3-HETEROARYL-ISO-(THIO)-UREAS

The invention relates to new 1-(2-oxyaminosulphonylphenylsulphonyl)-3-heteroaryl-iso-(thio)-ureas, inventive processes for their preparation, and their use as herbicides.

Various isourea and isothioureas have been disclosed as potential herbicides, but have not attained any great importance to date as agents for combating weeds and/or regulating plant growth (see DE-AS (German Published Specification) No. 1,138,039 and British Patent Specification No. 1,202,736).

New 1-(2-oxyaminosulphonylphenylsulphonyl)-3-heteroaryl-iso-(thio)-ureas of the general formula (I)

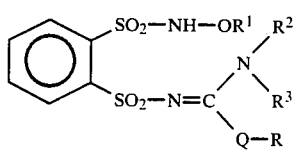
(I)

in which
R represents an optionally substitued radical from the series comprising alkyl, alkenyl, alkinyl, cycloalkyl-alkyl, cycloalkyl, aralkyl, aryl and hetaryl,
$R^1$ represents an optionally substituted radical from the series comprising alkyl, alkenyl, alkinyl, cycloalkyl, cycloalkyl-alkyl, aralkyl and aryl,
$R^2$ represents hydrogen or an optionally substituted radical from the series comprising alkyl, alkenyl, alkinyl and aralkyl,
$R^3$ represents an optionally substituted and/or optionally fused 6-membered aromatic heterocycle which contains at least one nitrogen atom, and
Q represents oxygen or sulphur,
and adducts of the compounds of the formula (I) with strong acids have now been found.

The new compounds of the formula (I) are obtained when (a) benzodisultams of the formula (II)

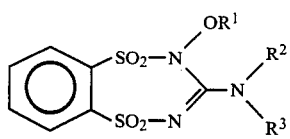
(II)

in which
$R^1$, $R^2$ and $R^3$ have the meanings given above, are reacted with compounds of the formula (III)

M—Q—R     (III)

in which
Q and R have the meanings given above and
M represents hydrogen or one equivalent of a metal, if appropriate in the presence of bases and, if appropriate, in the presence of diluents, and, if required, the products obtained in this step are treated with acids, or when (b) oxyguanidine derivatives of the formula (IV)

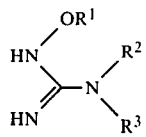
(IV)

in which
$R^1$, $R^2$ and $R^3$ have the meanings given above, are first reacted with benzene-1,2-disulphonyl dichloride of the formula (V)

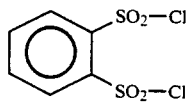
(V)

in the presence of acid acceptors and, if appropriate, in the presence of diluents, and then, without isolation of the reaction product of the formula (II)

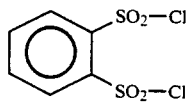
(II)

in which
$R^1$, $R^2$ and $R^3$ have the meanings given above, the reaction mixture is reacted with compounds of the formula (III)

M—Q—R     (III)

in which
Q and R have the meanings given above and
M represents hydrogen or one equivalent of a metal, if appropriate in the presence of bases and in presence of diluents, and, if required, the products obtained in this step are treated with acids.

The new sulphonyliso(thio)urea derivatives of the formula (I) and their adducts with strong acids are distinguished by pronounced herbicidal activity.

Surprisingly, the new compounds of the formula (I) have a substantially better herbicidal action than previously known isourea or isothiourea derivatives having the same direction of action.

It is furthermore to be regarded as surprising that the compounds according to the invention, of the formula (I), can be prepared by selective ring-opening of heterocycles of the formula (II), because, apart from this novel reaction, other ring-opening reactions, for example as a result of attack at the sulphonyl groupings, were also to be expected.

The invention preferably relates to compounds of the formula (I),
in which
R represents $C_1$-$C_{12}$-alkyl [which is optionally substituted by fluorine, chlorine, cyano, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkyl-carbonyl, $C_1$-$C_4$-alkoxy-carbonyl, $C_1$-$C_4$-alkylamino-carbonyl or di($C_1$-$C_4$-alkyl)-amino-carbonyl], $C_3$-$C_6$alkenyl, $C_3$-$C_6$-alkinyl, $C_3$-$C_6$-cycloalkyl, $C_3$-$C_6$-cycloalkyl-$C_1$- or $C_2$-alkyl, phenyl-$C_1$- or $C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl] or represents a phenyl radical which is optionally substituted by one or more radicals from the series comprising halogen [such as, in particular, fluorine, chlorine, bromine and iodine], cyano, nitro, hydroxyl, carboxyl, $C_1$–$C_6$-alkyl [which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl], $C_3$–$C_6$-cycloalkyl, $C_1$–$C_4$-alkoxy [which is optionally substituted by fluorine, chlorine, bromine, cyano, carboxyl, $C_1$–$C_4$-alkoxy, $C_1$–$C_4$-alkylthio or $C_1$–$C_4$-alkoxy-carbonyl], $C_1$–$C_4$-alkylthio [which is optionally substituted by fluorine, chlorine, bromine, cyano, carboxyl or $C_1$–$C_4$-alkoxy-carbonyl], amino, $C_1$–$C_4$-alkyl-amino or di-($C_1$–$C_4$-alkyl)-amino [which is optionally substituted by fluorine, chloride, bromine, cyano, carboxyl, $C_1$–$C_4$-alkoxy or $C_1$–$C_4$-alkoxy-carbonyl], $C_1$–$C_4$-alkylcarbonyl-amino, $C_1$–$C_4$-alkoxy-carbonyl-amino, (di)-$C_1$–$C_4$-alkylamino-carbonyl-amino, formyl, $C_1$–$C_4$-alkylcarbonyl, benzoyl, $C_1$–$C_4$-alkoxy-carbonyl, phenoxycarbonyl, benzyloxycarbonyl, phenyl [which is optionally substituted by fluorine, chlorine, bromine, cyano, nitro, hydroxyl or methyl], phenoxy, phenylthio, phenylsulphonyl, phenylamino or phenylazo [which are optionally substituted by fluorine, chlorine, bromine, cyano, nitro, methyl and/or trifluoromethyl], pyridyloxy or pyrimidyloxy [which are optionaly substituted by fluorine, chlorine, bromine, cyano, nitro, methyl and/or trifluoromethyl], $C_1$–$C_4$-alkyl-carbonyloxy, $C_1$–$C_4$-alkoxy-carbonyl-oxy, $C_1$–$C_4$-alkyl-aminocarbonyl-oxy and di-($C_1$–$C_4$-alkyl)-aminocarbonyloxy, or which is optionally fused to an alkylene chain [which is optionally branched and/or interrupted by one or more oxygen atoms] or a benzo radical [which is optionally substituted by fluorine, chlorine, bromine, cyano, nitro, methyl and/or trifluoromethyl];

wherein furthermore

R represents a 5-membered or 6-membered heteroaromatic ring which contains 1 to 3 nitrogen atoms and/or an oxygen or sulphur atom and which is optionally benzofused and/or substituted by fluorine, chlorine, bromine, cyano, nitro, $C_1$–$C_3$-alkyl or $C_1$–$C_3$-alkoxy [the last mentioned radicals optionally being substituted by fluorine and/or chlorine];

wherein furthermore $R^1$ represents $C_1$–$C_{12}$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl], $C_3$–$C_6$-alkenyl, $C_3$–$C_6$-alkinyl, $C_3$–$C_6$-cycloalkyl, $C_3$–$C_6$-cycloalkyl-$C_1$- or $C_2$-alkyl, phenyl-$C_1$- or $C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl] or phenyl [which is optionally substituted by fluorine, chlorine, nitro, cyano, $C_1$–$C_4$-alkyl, trifluoromethyl, $C_1$–$C_4$-alkoxy, $C_1$- or $C_2$-fluoroalkoxy, $C_1$–$C_4$-alkylthio, trifluoromethylthio or $C_1$–$C_4$-alkoxy-carbonyl], in which furthermore $R^2$ represents hydrogen, $C_1$–$C_4$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-amino-carbonyl], $C_3$–$C_6$-alkenyl, $C_3$–$C_6$-alkinyl or phenyl-$C_1$- or $C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl], in which furthermore $R^3$ represents the radical

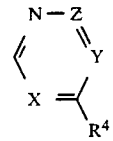

wherein $R^4$ represents hydrogen, fluorine, chlorine, bromine, hydroxyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino, $C_1$–$C_4$-alkylamino or di-($C_1$–$C_4$-alkyl)-amino, X represents nitrogen or a methine bridge (CH), Y represents nitrogen or an optionally substituted methine bridge C-$R^5$, wherein $R^5$ represents hydrogen, fluorine, chlorine, bromine or $C_1$–$C_4$-alkyl, and Z represents nitrogen or an optionally substituted methine bridge C-$R^6$, wherein $R^6$ represents hydroge, fluorine, chlorine, bromine, hydroxyl, $C_1$–$C_4$-alkyl [which is optionally substituted by flourine and/or chloride], $C_1$–$C_4$-alkoxy [which is optionally substituted by fluorine and/or chlorine], $C_1$–$C_4$-alkylthio [which is optionally substituted by fluorine and/or chlorine], amino, $C_1$–$C_4$-alkylamino or di-($C_1$–$C_4$-alkyl)-amino, and Q represents oxygen or sulphur.

The invention furthermore preferably relates to adducts of compounds of the formula (I)—as defined above—with hydrohalic acids, such as hydrogen fluoride, hydrogen chloride, hydrogen bromide or hydrogen iodide, with sulphuric acid, with alkanesulphonic acids which have 1 to 4 carbon atoms and are optionally substituted by fluorine and/or chlorine, or with benzenesulphonic or naphthalenesulphonic acids which are optionally substituted by fluorine, chlorine bromine or methyl.

The invention relates in particular to compounds of the formula (I)

in which

R represents $C_1$–$C_8$-alkyl [which is optionally substituted by fluorine or chlorine], $C_3$- or $C_4$-alkenyl, $C_1$- or $C_2$-alkoxy-carbonylmethyl, phenylethyl or benzyl [which is optionally substituted by fluorine, chlorine, nitro, cyano, methyl, methoxy or methoxy-carbonyl], or represents a phenyl radical which is optionally substituted by one or two radicals from the series comprising fluorine, chlorine, bromine, iodine, cyano, nitro, hydroxyl, carboxyl, $C_1$–$C_3$-alkoxy-carbonyl, $C_1$–$C_4$-alkyl, trifluoromethyl, hydroxymethyl, methoxycarbonylmethyl, phenyl-$C_1$-$C_3$-alkyl, cyclohexyl, $C_1$-$C_3$-alkoxy, trifluoromethoxy, $C_1$-$C_3$-alkylthio, trifluoromethylthio, dimethylamino, amino, acetylamino, methylaminocarbonyl, formyl, acetyl, benzoyl, phenyl, hydroxyphenyl, phenoxy, [which is optionally substituted by chlorine and/or trifluoromethyl], phenylamino, phenylazo and pyridyloxy [which is optionally substituted by chlorine and/or trifluoromethyl], or which is optionally benzofused;

and wherein furthermore $R^1$ represents $C_1$-$C_8$-alkyl [which is optionally substituted by fluorine or chlorine], $C_3$- or $C_4$-alkenyl, $C_1$- or $C_2$-alkoxy-carbonylmethyl, phenylethyl or benzyl [which is optionally substituted by fluorine, chlorine, nitro, cyano, methyl, methoxy or methoxy-carbonyl], $R^2$ represents hydrogen and $R^3$ represents the radical

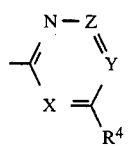

wherein $R^4$ represents chlorine, methyl, methoxy or ethoxy,

X represents nitrogen,

Y represents a methine bridge (CH), and

Z represents an optionally substituted methine bridge $C$-$R^6$, wherein $R^6$ represents hydrogen, chlorine, methyl, methoxy, ethoxy, methylthio, ethylthio, dimethylamino or diethylamino, and Q represents oxygen or sulphur.

The chemical reaction taking place in process (a) according to the invention can be represented by, for example, the following equation:

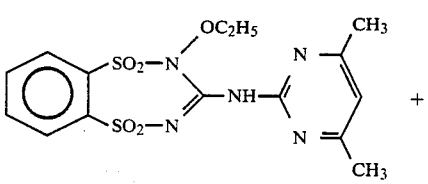

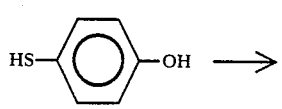

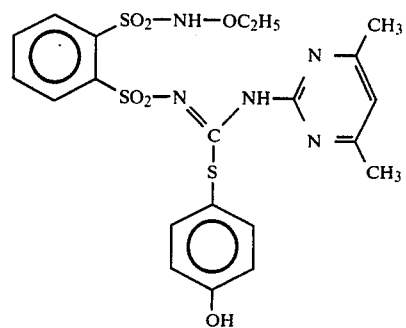

The chemical reaction taking place in process (b) according to the invention can be represented by, for example, the following equation:

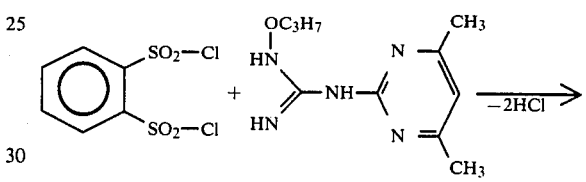

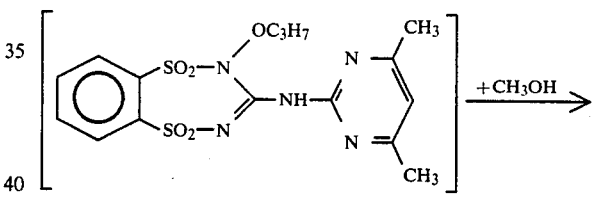

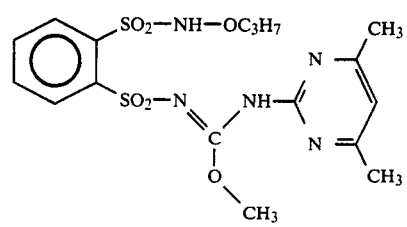

Formula (II) gives a general definition of the benzodisultams to be used as starting materials in process (a) according to the invention.

In formula (II), $R^1$, $R^2$ and $R^3$ preferably or particularly preferably have the same meanings as given above in connection with the definition of substituents for formula (I) as being preferred or particularly preferred, respectively.

Examples of starting materials of the formula (II) are listed in Table 1 below.

TABLE 1

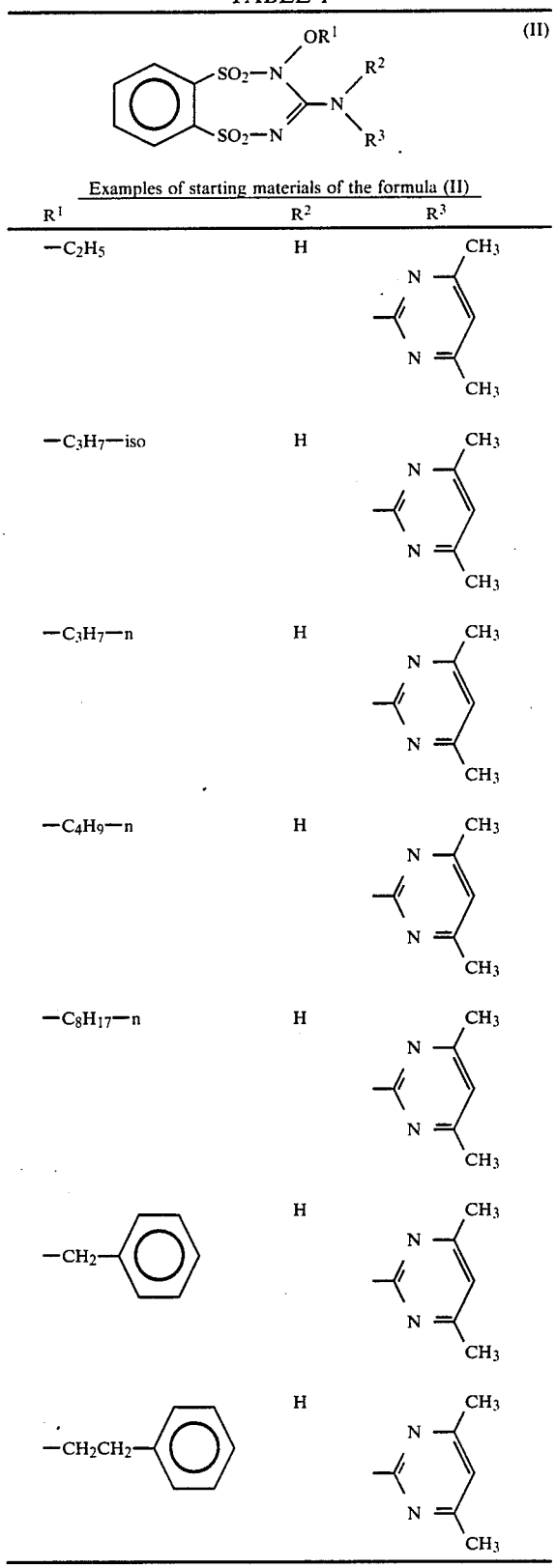

The compounds of the formula (II) have not been described in the literature to date. The compounds of the formula (II) are obtained when benzene-1,2-disulphonyl dichloride of the formula (V)

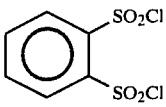

is reacted with oxyguanidine derivatives of the formula (IV)

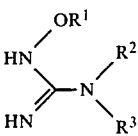

in which $R^1$, $R^2$ and $R^3$ have the meaning given above, in the presence of acid acceptors, such as, for example, pyridine or diazabicyclooctane (DABCO), and if appropriate in the presence of diluents, such as, for example, methylene chloride, chloroform, tetrahydrofuran or dioxane, at temperatures between $-30°$ C. and $+50°$ C.

Working-up can be carried out by customary methods, for example by evaporating down, taking up the residue in methylene chloride, washing the solution with dilute hydrochloric acid and with water, separating off, drying, filtering and evaporating down the organic phase, the products of the formula (II) remaining in the residue.

Benzene-1,2-disulphonyl dichloride of the formula (V), which is to be used as a starting material, is already known (see J. Org. Chem. 31, (1966), 3289–3292).

Formula (IV) gives a general definition of the oxyguanidine derivatives furthermore to be used as starting materials. In formula (IV), $R^1$, $R^2$ and $R^3$ preferably or particularly preferably have the same meanings as given above in connection with the definition of substituents for formula (I) as being preferred or particularly preferred, respectively.

The following may be mentioned as examples of starting materials of the formula (IV): N'-(4-methyl-pyrimidin-2-yl)-, N'-(4,6-dimethyl-pyrimidin-2-yl)-, N'-(4-methoxy-6-methyl-pyrimidin-2-yl)-, N'-(4-ethoxy-6-methyl-pyrimidin-2-yl)- , N'-(4-chloro-6-methoxy-pyrimidin-2-yl), N'-(4-chloro-ethoxy-pyrimidin-2-yl)-, N'-(4-chloro-6-dimethylamino-pyrimidin-2-yl)-, N'-(4-methyl-6-methylthio-pyrimidin-2-yl)- and N'-(4-dimethylamino-6-methyl-pyrimidin-2-yl)-N''-methoxy-guanidine, -N''-ethoxyguanidine, -N''-propoxy-guanidine, -N''-isopropoxyguanidine, -N''-butoxy-guanidine, -N''-isobutoxy-guanidine, -N''-sec.-butoxy-quanidine, -N''-pentoxy-guanidine, -N''-isopentoxy-guanidine, -N''-hexyloxy-guanidine, -N''-octyloxy-guanidine, -N''-allyloxy-guanidine, -N''-(2-chloro-ethoxy)-guanidine, -N''-(2-fluoro-ethoxy)-guanidine, -N''-(2-chloro-propoxy)-guanidine, -N''-(2-fluoro-propoxy)-guanidine, -N''-(3-chloro-propoxy)-guanidine, -N''-(4-chloro-butoxy)-guanidine, -N''-methoxycarbonylmethoxy-guanidine, -N''-ethoxycarbonyl-methoxy-guanidine, -N''-(1-methoxycarbonyl-ethoxy)-guanidine, -N''-(1-ethoxycarbonylethoxy)-guanidine, -N''-dimethylaminocarbonylmethoxy-guanidine, -N''-(2-phenylethoxy)-guanidine, -N''-phenoxy-guanidine, -N''-(4-methylbenzyloxy)-guanidine, -N''-(4-fluoro-benzyloxy)-guanidine, -N''-(4-chloro-benzyloxy)-guanidine, -N''-(4-nitrobenzyloxy)-guanidine, -N''-(2,6-dichloro-benzyloxy)-guanidine, -N"-(4-methoxycarbonyl-benzoyloxy)-guanidine and -N"-(4-ethoxycarbonyl-benzyloxy)-guanidine.

Some of the starting materials of the formula (IV) are known (see J. Chem. Soc. 1962, 3915); some of them form the subject of commonly assigned patent application Serial No. 578,345, filed Feb. 9, 1984, now pending, corresponding to DE-OS (German Published Specification) No. 3,334,455.

The compounds of the formula (IV) are obtained when cyanamide derivatives of the formula (VI)

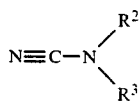  (VI)

in which
R² and R³ have the meanings given above, are reacted with hydroxylamine derivatives of the formula (VII)

H₂N—OR¹  (VII)

in which
R¹ has the meaning given above, or with hydrochlorides of hydroxylamine derivatives of the formula (VII), if appropriate in the presence of diluents, such as, for example, ethanol, propanol or butanol, at temperatures between 20° C. and 120° C., and, if required, the reaction products are treated with acid acceptors, such as, for example, ammonia, potassium carbonate or sodium hydroxide.

Some of the cyanamide derivatives of the formula (VI) are known (see J. Chem. Soc. 1953, 1725). The compounds of the formula (VI) are essentially obtained by the following synthesis routes:

(a) by reacting alkali metal or alkaline earth metal salts of cyanamide—such as, for example, sodium cyanamide or calcium cyanamide—with chloro-hetarenes of the formula (VIII)

Cl—R³  (VIII)

in which
R³ has the meaning given above, and, if required, then—when R² does not represent hydrogen—reacting the product with halogen compounds of the formula (IX)

T—R²  (IX)

in which
R² represents an optionally substituted radical from the series comprising alkyl, alkenyl, alkinyl and aralkyl, and
T represents chlorine, bromine or iodine,
if appropriate in the presence of inert diluents, such as, for example, acetone, acetonitrile or dimethylformamide, at temperatures between 0° C. and 100° C.

After the mixture has been evaporated down and the residue dissolved in water, the cyanamide derivatives of the formula (VI) can be precipitated by acidification (for example with hydrochloric acid), and isolated by being filtered off under suction.

Alternatively, the compounds of the formula (VI) are obtained (b) in the case in which R³ represents a substituted pyrimidyl radical, by reaction of cyanoguanidine ("Dicyanodiamide") with β-dicarbonyl compounds, such as acetylacetone (see J. Chem. Soc. 1953, 1725–1730), acetoacetates (see J. Prakt. Chem. 77 (1908), 542 and J. Chem. Soc. 1948, 586) or malonates (see German Patent Specification 158,591).

The 2-cyanomino-4-hydroxy-6-methyl- or 4,6-dihydroxy-pyrimidines obtained from acetoacetates or malonates can be converted to the corresponding 2-cyanoamino-4-alkoxy-6-methyl- or -4,6-dialkoxy-pyrimidines in a conventional manner, by reacting with alkylating agents, such as, for example, dimethyl or diethyl sulphate, if appropriate in the presence of diluents, such as, for example, water, methanol, ethanol, n- and iso-propanol, acetone, dioxane or dimethylformamide, and in the presence of acid-binding agents, such as, for example, sodium hydroxide, potassium hydroxide, sodium carbonate or potassium carbonate. If necessary, in order to avoid N-alkylation, acylation with an acylating agent, such as, for example, acetic anhydride or acetyl chloride, is carried out, and, after the alkylation, deacylation is once again effected with aqueous acids or bases.

In another alternative process, the compounds of the formula (VI) are obtained when
(c) amino-hetarenes of the formula (X)

H₂N—R³  (X)

in which R³ has the meaning given above, are reacted with carbonyl isothiocyanates of the formula (XI)

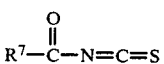  (XI)

in which
R⁷ represents ethoxy or phenyl, if appropriate in the presence of an inert diluent, such as, for example, acetone, acetonitrile or toluene, at temperatures between 0° C. and 100° C., the carbonylthioureas formed in this procedure, of the formula (XII)

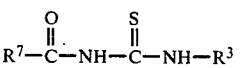  (XII)

in which
R³ and R⁷ have the meaning given above, are isolated by being filtered off under suction, if necessary after the mixture has been evaporated down, and are reacted with aqueous alkali metal or alkaline earth metal hydroxide solutions, such as, for example, sodium hydroxide solution, if appropriate in the presence of an organic solvent, such as, for example, tetrahydrofuran or dioxane, at temperatures between 0° C. and 120° C., and the thioureas of the formula (XIII)

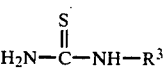  (XIII)

in which
R³ has the meaning given above, which are obtained in crystalline form after acidification, for example with hydrochloric acid, are isolated by being filtered off under suction, and reacted with metal compounds which can bind hydrogen sulphide such as, for example, lead (II) acetate, copper (II) acetate, mercury (II) actetate or iron (II) acetate, in the presence of aqueous alkali metal or alkaline earth metal hydroxide solutions, such as, for example, sodium hydroxide solution, at temperatures between 20° C. and 100° C., and, when the reaction is complete, the mixture is filtered and the filtrate is acidified with an acid, such as, for example, acetic acid. The products of the formula (VI) which are obtained in crystalline form in this procedure can be isolated by being filtered off under suction.

The starting material for the preparation processes described above under (a), (b) and (c) for the cyanamide derivatives of the formula (VI) are known and/or can be prepared by processes which are in themselves known.

These include the chloro-hetarenes of the formula (VIII) (see J. Chem. Soc. (c) 1966, 2031; Chem. Pharm. Bull. 11 (1963), 1382–1388 and Arch. Pharm. 295, (1962), 649–657), the halogen compounds of the formula (IX) (commercial chemicals), the amino-hetarenes of the formula (X) (see Chem. Pharm. Bull. 11, (1963), 1382–1388; J. Chem. Soc. 1946, 81 and U.S. Pat. No. 4,299,960), and the carbonylisothiocyanates of the formula (XI) (see J. Heterocycl. Chem. 5 (1968), 837 and U.S. Pat. No. 4,160,037).

Formula (III) gives a general definition of the compounds furthermore to be used as starting materials in process (a) according to the invention. In formula (III), Q and R preferably or particularly preferably have the same meanings as mentioned above in connection with the definition of substituents for formula (I) as being preferred or particularly preferred, and M preferably and particularly represents hydrogen, sodium or potassium.

The following may be mentioned as examples of the starting materials of the formula (III): methanol, ethanol, propanol, isopropanol, butanol, isobutanol, allyl alcohol, propargyl alcohol, benzyl alcohol, methyl glycolate, methyl lactate, phenyl, 2-, 3- and 4-fluorophenol, 2-, 3- and 4-chlorophenol, 2-, 3- and 4-bromophenol, 4-iodo-phenol, 2,3-dichloro-phenol, 2,4-dichloro-phenol, 2,5-dichloro-phenol, 4-cyanophenol, 2-, 3- and 4-nitro-phenol, 4-chloro-3-nitro-phenol, 3-chloro-4-nitro-phenol, pyrocatechol (1,2-dihydroxybenzene), resorcinol (1,3-dihydroxy-benzene), hydroquinone (1,4-dihydroxy-benzene), 2-, 3- and 4-hydroxybenzoic acid, 2-, 3- and 4-methyl-phenol, 3,4-dimethylphenol, 3,5-dimethyl-phenol, 4-isopropyl-phenol, 4-tert.-butyl-phenol, 4-chloro-3,5-dimethyl-phenol, 4-hydroxy-benzyl alcohol, 3-methyl-4-nitro-phenol, 4-chloro-3-methyl-phenol, 3- and 4-trifluoromethylphenol, methyl-4-hydroxy-phenylacetate, 4-(1-methyl-1-phenyl-ethyl)-phenol, 4-cyclohexyl-phenol, methyl and ethyl 3- and 4-hydroxy-benzoate, 2-, 3- and 4-methoxy-phenol, 4-trifluoromethoxy-phenol, 4-methylthio-phenol, 3-methyl-4-methylthio-phenol, 4-trifluoromethylthio-phenol, 3-dimethylamino-phenol, 3-methyl-4-dimethylamino-phenol, 4-methyl-3-dimethylamino-phenol, 4-acetylamino-phenol, 3-hydroxy and 4-hydroxy-benzaldehyde, 4-hydroxy-acetophenone, 4-hydroxy-benzophenone, 4-hydroxy-biphenyl, 4,4'-bis-hydroxy-bisphenyl, 1-naphthol, 2-naphthol, 3-hydroxy-biphenyl, 4-hydroxy-azobenzene, 4-hydroxy-diphenylamine, 3-hydroxy-diphenylamine, 3-phenoxyphenol, 4-phenoxy-phenol, 4-(2,4-dichloro-phenoxyphenol, 4-(4-trifluoromethyl-phenoxy)-phenol, 4-(3,5-dichloro-2-pyridoxy)-phenol, 4-(3-chloro-5-trifluoromethyl-2-pyridoxy)-phenol, methanethiol, ethanethiol, propanethiol, 1-methyl-ethanethiol, butanethiol, 1-methyl-propanethiol, 2-methyl-propanethiol, phenylmethanethiol, thiophenol, 4-chloro-thiophenol, 4-methyl-thiophenol, 2-amino-thiophenol, 3-amino-thiophenol, 4-amino-phenol, 2-amino-thiophenol, 3-amino-thiophenol, 4-methoxy-thiophenol, 2-mercapto-benzoic acid and 4-hydroxy-thiophenol, and the sodium and potassium salts of these compounds.

The starting materials of the formula (III) are known products which are substantially commercially available.

The benzene-1,2-disulphonyl dichloride of the formula (V) which is to be used as a starting material in process (b) according to the invention is already known (see J. Org. Chem. 31, (1966), 3289–3292).

Formula (IV) gives a general definition of the oxyguanidine derivatives to be used as starting materials in process (b) according to the invention. In formula (IV), $R^1$, $R^2$ and $R^3$ preferably or particularly preferably have the same meanings as stated above in connection with the definition of substituents for formula (I) as being preferred or particularly preferred, respectively. Examples of compounds of the formula (IV) have already been mentioned above in connection with the description of the starting materials for process (b). The preparation of the starting materials of the formula (IV) has already been described in connection with the description of the starting materials for process (a).

Formula (III) gives a general definition of the compounds furthermore to be used as starting materials in process (b) according to the invention. In formula (III), Q and R preferably or particularly preferably have the same meanings as mentioned above in connection with the definition of substituents for the formula (I) as being preferred or particularly preferred, respectively, and M preferably and particularly represents hdyrogen, sodium or potassium.

Examples of compounds of the formula (III) have already been mentioned above in connection with the description of the starting materials for process (a).

Process (a) according to the invention, for the preparation of the new compounds of the formula (I), is preferably carried out using diluents. Suitable diluents are virtually all organic solvents. These include optionally halogenated hydrocarbons, such as, for example, methylene chloride, chloroform, toluene and chlorobenzene, ethers, such as, for example, diethyl ether, tetrahydrofuran, dioxane and 1,2-dimethoxyethane, nitriles, such as, for example, acetonitrile and propionitrile, and dimethylformamide, dimethylacetamide, dimethyl sulphoxide and sulpholane. The alcohols falling under formula (III), such as, for example, methanol, ethanol, propanol and isopropanol, can, if required—provided that they are employed as reactants—also be used as diluents.

Process (a) is, if appropriate, carried out in the presence of bases. Suitable bases are virtually all conventionally used acid-binding agents. These include, in particular, metal hydroxides, carbonates, hydrides and alcoholates, such as, for example, sodium, potassium and calcium hydroxide, potassium carbonate, sodium and calcium hydride, sodium methylate, ethylate and propylate, potassium methylate, ethylate and tert.-butylate and aluminum isopropylate, as well as nitrogen heterocycles, such as, for example pyrazole. The products formed in process (a) are, if appropriate, treated with acids. A very large variety of proton donors are suitable, such as, for example, hydrochloric acid, sulphuric acid, phosphoric acid, formic acid, acetic acid, carbonic acid, sodium bicarbonate, ammonium carbonate and water.

In process (a) according to the invention, the reaction temperatures can be varied within a relatively wide range. In general, the reaction is carried out at temperatures between 0° C. and 150° C., preferably between 10° C. and 100° C. The process according to the invention is carried out in general under atmospheric pressure.

To carry out process (a), in general between 1 and 100 mols, preferably between 1 and 10 mols, of the compound of the formula (III) are employed per mol of benzodisultams of the formula (II). The reactants are usually combined at room temperature or with external cooling, and the reaction mixture is stirred until the reaction is complete, if appropriate at elevated temperature. Working-up and isolation of the new compounds are carried out by customary methods:

For example, the reaction mixture—if appropriate, after being stirred with a virtually water-immiscible solvent, such as, for example, methylene chloride-is washed with dilute hydrochloric acid and with water, dried, filtered and evaporated down. The product of the formula (I) which remains in the residue is crystallized by trituration with a suitable organic solvent, such as, for example, ethanol, and is isolated by being filtered off under suction.

Process (b) according to the invention, for the preparation of the new compounds of the formula (I), is preferably carried out using diluents. Suitable diluents are virtually all inert organic, preferably aprotic polar solvents. These include optionally substituted hydrocarbons, such as, for example, methylene chloride, chloroform, 1,2-dichloroethane, toluene, xylene and chlorobenzene, nitriles, such as, for example, acetonitrile and propionitrile, ethers, such as, for example, 1,2-dimethoxyethane, tetrahydrofuran and dioxane, and dimethylformamide, dimethylacetamide, dimethyl sulphoxide, sulpholane, pyridine and 2-methyl-5-ethyl-pyridine.

Virtually all customarily used acid-binding agents can be employed as acid acceptors in process (b). These include, in particular, alkali metal and alkaline earth metal hydroxides, alkali metal and alkaline earth metal hydrides, organometallic compounds, such as butyllithium, as well as aliphatic, aromatic or heterocyclic amines, such as trimethylamine, triethylamine, N,N-dimethylaniline, N,N-dimethyl-benzylamine, diazabicyclooctane (DABCO), diazabicyclononene (DBN), diazabicycloundecene (DBU), pyridine, 2-methyl-5-ethyl-pyridine and 4-dimethylaminopyrindine.

In process (b), the reaction temperatures can be varied within a relatively wide range. In general, the reaction is carried out at between $-80°$ and $+150°$ C., preferably between $-30°$ and $+100°$ C. Process (b) according to the invention is carried out in general under atmospheric pressure.

To carry out process (b), in general between 1 and 2 mols, preferably between 1.0 and 1.2 mols, of benzene-1,2-disulphonyl dichloride of the formula (V) and then between 1 and 100 mols, preferably between 5 and 10 mols, of the compound of the formula (III) are employed per mol of the oxyguanidine derivative of the formula (IV).

The reactants are usually combined at room temperature or with external cooling, and the reaction mixture is stirred until the reaction is complete.

Working-up can be carried out in a customary manner; for example, by a method in which the mixture is, if required, evaporated down and/or diluted with a virtually water-immiscible organic solvent, such as, for example, methylene chloride, washed with dilute hydrochloric acid and with water, dried, filtered and evaporated down. The product of the formula (I) which remains in the residue is crystallized by trituration with a suitable organic solvent, such as, for example, ethanol, and is isolated by being filtered off under suction.

The active compounds according to the invention can be used as defoliants, desiccants and agents for destroying broad-leaved plants, and especially as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotinana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochloria, Fimbristylis, Sagittaria, Eleocharis, Scirpus, Paspalum, Ischaemum, Sphenoclea, Dactyloctenium, Agrostis, Alopecurus and Apera.

Monycotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber planatations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixtures being possible.

Suitable herbicides for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5-(4H)-one, 2-chloro-4-ethylamino-6-isopropyl-amino-1,3,5-triazine, the R enantiomer of (trimethylsilyl)-methyl 2-[4-(3,5-dichloropyridin-2-yloxy)-phenoxy]-propionate, the R enantiomer of (2-benzyloxy)-ethyl 2-[4-(3,5-dichloropyrid-2-yloxy)-phenoxy]-propionate, 2,4-dichlorophenoxy-acetic acid, 2-(2,4-dichlorophenoxy)-propionic acid, 4-chloro-2-methyl-phenoxy-acetic acid, 2-(2-methyl-4-chlorophenoxy)-propionic acid, 3,5-diiodo-4-hydroxy-benzonitrile, 3,5-dibromo-4-hydroxy-benzonitrile and diphenyl ether and phenylpyridazines, such as, for example, pyridates. Surprisingly, some mixtures also have a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil area, preferably between 0,05 and 5 kg per ha.

The preparation and the use of the active compounds according to the invention are described in the Examples below.

PREPARATION EXAMPLES

EXAMPLE 1

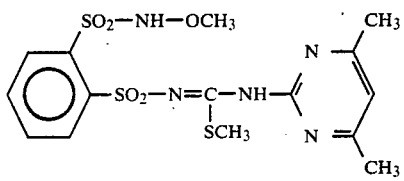

(Process (b))

6.9 g (0.025 mol) of benzene-1,2-disulphonyl dichloride are added in portions, at −20° C., to a mixture of 4.9 g (0.025 mol) of N'-(4,6-dimethyl-pyrimidin-2-yl)-N''-methoxy-guanidine, 6 g (0.087 mol) of pyridine and 80 ml of methylene chloride. Stirring is continued for 3 hours at −20° C. and for 15 hours at +20° C.

1.2 g (0.025 mol) of methylmercaptan are then added to the reaction mixture, and stirring is continued for 5 hours at 20° C. Thereafter the solvent is stripped off and the residue is triturated with a small amount of alcohol. The product obtained in crystalline form in this procedure is isolated by being filtered off under suction. 8 g (71% of theory) of N'-(4,6-dimethylpyrimidin-2-yl)-N''-(2-methoxyaminosulphonylphenylsulphonyl)-S-methylisothiourea of melting point 201° C. are obtained.

EXAMPLE 2

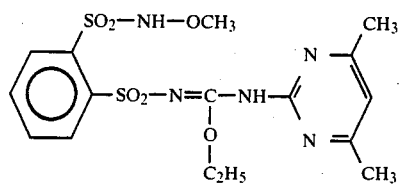

(Process (a))

A solution of 7 g (0.0175 mol) of the compound of the structural formula

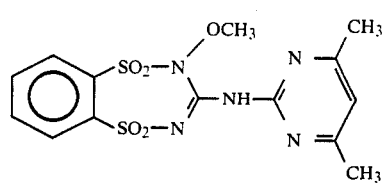

in 30 ml of ethanol is heated under reflux for 4 hours. Thereafter, the mixture is partially evaporated down, and the product obtained in crystalline form is isolated by being filtered off under suction.

After recrystallization from acetonitrile, 5.4 g (71% of theory) of N'-(4,6-dimethyl-pyrimidin-2-yl)-N''-(2-methoxyaminosulphonylphenylsulphonyl)-O-ethyl-iso-urea of melting point 170°–171° C. are obtained.

EXAMPLE 3

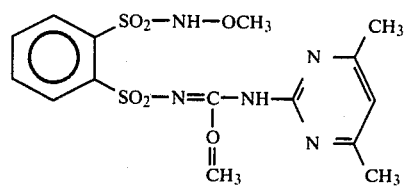

Process (a))

A mixture of 4.8 g (0.012 mol) of the compound of the structural formula below

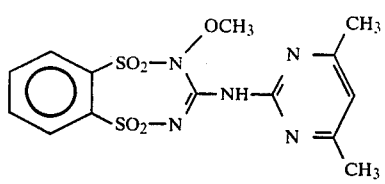

0.82 g (0.012 mol) of pyrazole and 30 ml of methanol is stirred for 18 hours at 20° C. The product obtained in crystalline form is isolated by being filtered off under suction and is dried.

5.1 g (97% of theory) of N'-(4,6-dimethylpyrimidin-2-yl)-N''-(2-methoxyaminosulphonylphenylsulphonyl)-O-methyl-iso-urea of melting point 163°–165° C. are obtained.

The compounds of the formula (I) which are listed in Table 2 below can be prepared by the processes described, by way of example, in the examples above:

TABLE 2

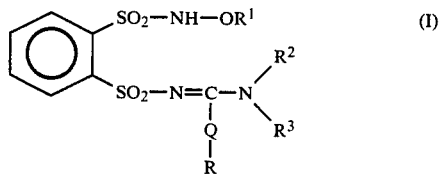

| Example No. | R | R$^1$ | R$^2$ | R$^3$ | Q | Melting point (°C.) |
|---|---|---|---|---|---|---|
| 4 | phenyl | —CH$_3$ | H | 4,6-dimethylpyrimidin-2-yl | S | 188 (decomposition) |
| 5 | phenyl | —CH$_3$ | H | 4,6-dimethylpyrimidin-2-yl | O | |
| 6 | phenyl | —n-C$_4$H$_9$ | H | 4,6-dimethylpyrimidin-2-yl | S | 141 |

TABLE 2-continued
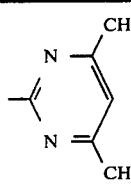
| Example No. | R | R¹ | R² | R³ | Q | Melting point (°C.) |
|---|---|---|---|---|---|---|
| 7 | $-C_2H_5$ | $-i-C_3H_7$ | H | 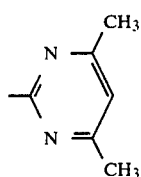 | O | 161 |
| 8 | $-CH_3$ | $-n-C_3H_7$ | H | 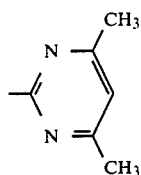 | O | |
| 9 | $-CH_3$ | $-C_8H_{17}$ | H | 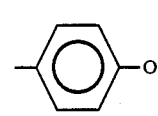 | S | |
| 10 | 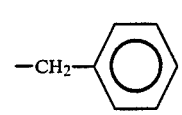 | $-CH_2$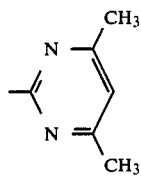 | H | 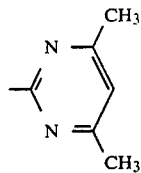 | S | |
| 11 | $-CH_3$ | $-C_2H_5$ | H | 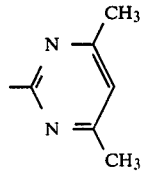 | O | |
| 12 | $-CH_3$ | $-C_2H_5$ | H | 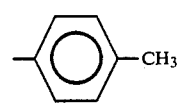 | S | |
| 13 | 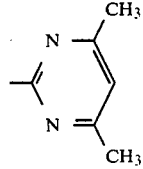 | $-C_2H_5$ | H | (pyrimidine) | S | |

TABLE 2-continued
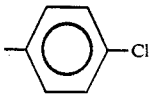
| Example No. | R | $R^1$ | $R^2$ | $R^3$ | Q | Melting point (°C.) |
|---|---|---|---|---|---|---|
| 14 | 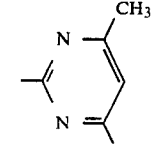 | $-C_2H_5$ | H | 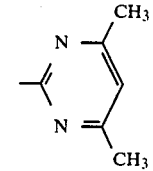 | O | |
| 15 | $-CH_3$ | $-CH_2COOC_2H_5$ | H | 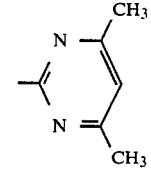 | S | |
| 16 | $-C_2H_5$ | $-CH(CH_3)_2$ | H | 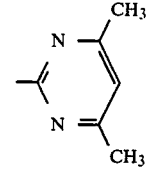 | O | 161 |
| 17 | $-C_2H_5$ | $-C_3H_7-n$ | H | 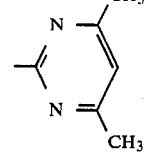 | O | 131 |
| 18 | $-C_2H_5$ | $-C_2H_5$ | H | 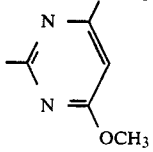 | O | 209 |
| 19 | $-CH_3$ | $-CH_3$ | H | 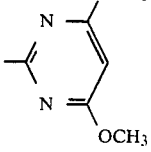 | O | |
| 20 | $-C_2H_5$ | $-CH_3$ | H |  | O | |

TABLE 2-continued $$\text{(I)}$$

Structure: benzene ring with $SO_2-NH-OR^1$ and $SO_2-N=C(-Q-R)-NR^2R^3$ substituents.

| Example No. | R | $R^1$ | $R^2$ | $R^3$ | Q | Melting point (°C.) |
|---|---|---|---|---|---|---|
| 21 | 4-hydroxyphenyl | $-C_2H_5$ | H | 4,6-dimethoxypyrimidin-2-yl | S | |
| 22 | $-C_2H_5$ | $-C_2H_5$ | H | 4,6-dimethoxypyrimidin-2-yl | O | |
| 23 | $-CH_3$ | $-CH_3$ | H | 4-methyl-6-methoxypyrimidin-2-yl | O | |
| 24 | $-C_2H_5$ | $-CH_3$ | H | 4-methyl-6-methoxypyrimidin-2-yl | O | |
| 25 | 4-tert-butylphenyl | $-CH_3$ | H | 4-methyl-6-methoxypyrimidin-2-yl | O | |
| 26 | 4-hydroxyphenyl | $-CH_3$ | H | 4-methyl-6-methoxypyrimidin-2-yl | S | |
| 27 | $-CH_3$ | $-C_2H_5$ | H | 4,6-dimethoxypyrimidin-2-yl | O | |

TABLE 2-continued $$\text{(I)} \quad \underset{\underset{\overset{|}{\underset{R}{O}}}{SO_2-N=C-N}}{\overset{SO_2-NH-OR^1}{\bigotimes}}\overset{R^2}{\underset{R^3}{<}}$$

| Example No. | R | $R^1$ | $R^2$ | $R^3$ | Q | Melting point (°C.) |
|---|---|---|---|---|---|---|
| 28 | —CH₃ | —C₂H₅ | H | 4-methoxy-6-methylpyrimidin-2-yl | O | |
| 29 | —CH₃ | —CH₂CH=CH₂ | H | 4-methoxy-6-methylpyrimidin-2-yl | O | |
| 30 | —CH₃ | —CH₃ | H | 4-methylpyrimidin-2-yl | O | |
| 31 | —C₂H₅ | —CH₃ | H | 4-methylpyrimidin-2-yl | O | |
| 32 | 4-hydroxyphenyl | —CH₃ | H | 4-methylpyrimidin-2-yl | S | |
| 33 | —CH₃ | —C₂H₅ | H | 4-ethylpyrimidin-2-yl | O | |
| 34 | —CH₃ | —CH₃ | H | 4,6-dimethylpyridin-2-yl | O | |
| 35 | —CH₃ | —CH₃ | H | 4-difluoromethoxy-6-methylpyrimidin-2-yl | O | |

TABLE 2-continued

Structure (I): benzene with SO$_2$—NH—OR$^1$ and SO$_2$—N=C(—N R$^2$R$^3$)—O—R (with Q at C)

| Example No. | R | R$^1$ | R$^2$ | R$^3$ | Q | Melting point (°C.) |
|---|---|---|---|---|---|---|
| 36 | —CH$_3$ | —CH$_3$ | H | 4-OCH$_3$-6-Cl-pyrimidin-2-yl | O | |
| 37 | —CH$_3$ | —CH$_3$ | H | 4-CH$_3$-6-Cl-pyrimidin-2-yl | O | |
| 38 | —CH$_3$ | —CH$_3$ | —CH$_3$ | 4-CH$_3$-6-OCH$_3$-pyrimidin-2-yl | O | |
| 39 | —CH$_3$ | —CH$_3$ | H | 4-CH$_3$-6-OC$_2$H$_5$-pyrimidin-2-yl | O | |

Preparation of starting materials of the formula (II)

EXAMPLE (II-1)

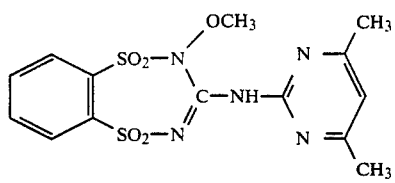

14 g (0.05 mol) of benzene-1,2-disulphonyl dichloride are added in portions, at −20° C., to a mixture of 10 g (0.05 mol) of N'-(4,6-dimethylpyrimidin-2-yl)-N"-methoxyguanidine, 12 g (0.15 mol) of pyridine and 100 ml of methylene chloride. Stirring is continued for 3 hours at −20° C. and for 15 hours at +20° C.

Thereafter, the reaction mixture is washed with ice-cooled dilute hydrochloric acid and ice water. The methylene chloride solution is dried and evaporated down. The residue is triturated with ethanol. The residue obtained in crystalline form in this procedure is isolated by being filtered off under suction.

11.5 g (15% of theory) of the compound of the structural formula given above and of melting point 158° C. (decomposition) are obtained.

Working-up of the reaction mixture can also be carried out by completely evaporating down the mixture when the reaction is complete, pre-grinding the residue with ethanol, and isolating the disultam having the above structure by filtering it off under suction.

The compounds of the formula (II) which are listed in Table 3 below can be prepared by the processes described, by way of example, in Example II-1 above:

TABLE 3

Structure (II): benzene with SO$_2$N(—O—R$^1$)—C(=N SO$_2$)—N R$^2$R$^3$

| Example No. | R$^1$ | R$^2$ | R$^3$ | Melting point (°C.) |
|---|---|---|---|---|
| (II-2) | —C$_2$H$_5$ | H | 4,6-dimethylpyrimidin-2-yl | 104 (decomposition) |

TABLE 3-continued structure (II): benzene ring fused with -SO₂N(O-R¹)-C(=NSO₂-)-N(R²)(R³)

| Example No. | R¹ | R² | R³ | Melting point (°C.) |
|---|---|---|---|---|
| (II-3) | —C₃H₇i | H | 4,6-dimethylpyrimidin-2-yl | amorphous |
| (II-4) | —C₃H₇n | H | 4,6-dimethylpyrimidin-2-yl | 134 |
| (II-5) | —C₄H₉n | H | 4,6-dimethylpyrimidin-2-yl | 179 (decomposition) |
| (II-6) | —C₈H₁₇n | H | 4,6-dimethylpyrimidin-2-yl | 164 |
| (II-7) | —CH₂—C₆H₅ | H | 4,6-dimethylpyrimidin-2-yl | 198 |
| (II-8) | —CH₂CH₂—C₆H₅ | H | 4,6-dimethylpyrimidin-2-yl | |
| (II-9) | —CH₂CH(CH₃)₂ | H | 4,6-dimethylpyrimidin-2-yl | |
| (II-10) | —CH₂CH=CH₂ | H | 4,6-dimethylpyrimidin-2-yl | 180 |
| (II-11) | —CH₃ | —CH₃ | 4,6-dimethylpyrimidin-2-yl | |
| (II-12) | —CH₃ | —CH₃ | 4-methyl-6-methoxypyrimidin-2-yl | |
| (II-13) | —CH₃ | H | 4,6-dimethylpyrimidin-2-yl | |
| (II-14) | —CH₃ | H | 4-methyl-6-ethylpyrimidin-2-yl | |
| (II-15) | —CH₂COOC₂H₅ | H | 4,6-dimethylpyrimidin-2-yl | 210 (decomposition) |
| (II-16) | —CH(CH₃)₂ | H | 4,6-dimethylpyrimidin-2-yl | |
| (II-17) | —CH₃ | H | 4,6-dimethylpyrimidin-2-yl | |

TABLE 3-continued (II)

| Example No. | $R^1$ | $R^2$ | $R^3$ | Melting point (°C.) |
|---|---|---|---|---|
| (II-18) | —CH$_3$ | H | (4-methyl-6-difluoromethoxy-pyrimidin-2-yl) | |
| (II-19) | —CH$_3$ | H | (4,6-dimethoxy-pyrimidin-2-yl) | |
| (II-20) | —C$_2$H$_5$ | H | (4,6-dimethoxy-pyrimidin-2-yl) | |
| (II-21) | —CH$_2$CH(CH$_3$)$_2$ | H | (4,6-dimethoxy-pyrimidin-2-yl) | |
| (II-22) | —CH$_3$ | H | (4-methyl-6-methoxy-pyrimidin-2-yl) | 151 |

TABLE 3-continued (II)

| Example No. | $R^1$ | $R^2$ | $R^3$ | Melting point (°C.) |
|---|---|---|---|---|
| (II-23) | —CH$_2$CH=CH$_2$ | H | (4-methyl-6-methoxy-pyrimidin-2-yl) | |
| (II-24) | —CH$_3$ | H | (4-methyl-6-ethoxy-pyrimidin-2-yl) | |

Preparation of starting materials of the formula (IV)

EXAMPLE (IV-1)

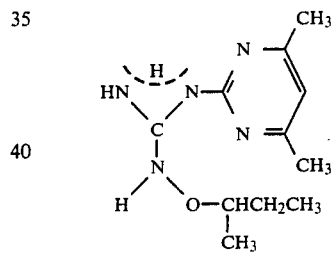

A mixture of 143 g of (0.97 mol) of 2-cyanoamino-4,6-dimethyl-pyrimidine, 94.3 g (1.06 mols) of O-sec.-butyl-hydroxylamine and 190 ml of ethanol is heated to the boil under reflux for 6 hours. Thereafter, the mixture is filtered under suction, the filtrate is evaporated down, and 500 ml of water are added to the residue. The product obtained in crystalline form in this procedure is isolated by being filtered off under suction.

131 g (57% of theory) of N'-(4,6-dimethyl-pyrimidin-2-yl)-N''-sec.-butoxy-guanidine of melting point 78° C. are obtained.

The compounds of the formula (IV) which are listed in Table 4 below can be prepared analogously:

TABLE 4

$$\begin{array}{c} \text{O}-\text{R}^1 \\ \text{HN} \diagdown \diagup \text{R}_2 \\ \text{C}-\text{N} \\ \text{HN} \diagup \diagdown \text{R}_3 \end{array}$$

| Example No. | R$^1$ | R$^2$ | R$^3$ | Melting point (°C.) |
|---|---|---|---|---|
| (IV-2) | —CH$_2$CH(CH$_3$)$_2$ | H | 4,6-dimethylpyrimidin-2-yl (2-methyl) | 52 |
| (IV-3) | —CH$_2$CH=CH$_2$ | H | 4,6-dimethylpyrimidin-2-yl | 103 |
| (IV-4) | —CH(CH$_3$)$_2$ | H | 4,6-dimethylpyrimidin-2-yl | 84 |
| (IV-5) | —CH$_2$—CH$_2$—C$_6$H$_5$ | H | 4,6-dimethylpyrimidin-2-yl | $n_D^{24}$ = 1.5776 |
| (IV-6) | n-C$_4$H$_9$ | H | 4,6-dimethylpyrimidin-2-yl | (oil) |
| (IV-7) | n-C$_8$H$_{17}$ | H | 4,6-dimethylpyrimidin-2-yl | 58 |
| (IV-8) | —CH$_2$—(2-chlorophenyl) | H | 4,6-dimethylpyrimidin-2-yl | 102–103 |
| (IV-9) | —CH$_2$CH$_2$CH$_2$Cl | H | 4,6-dimethylpyrimidin-2-yl | 137 |

TABLE 4-continued $$\begin{array}{c} \text{HN} \overset{\text{O—R}^1}{\underset{\text{HN}}{\diagup}} \text{N} \overset{R_2}{\underset{R_3}{\diagdown}} \end{array}$$

| Example No. | R$^1$ | R$^2$ | R$^3$ | Melting point (°C.) |
|---|---|---|---|---|
| (IV-10) | —C$_6$H$_5$ (phenyl) | H | 4,6-dimethylpyrimidin-2-yl | 189–192 (decomposition) |
| (IV-11) | —CH$_2$COOCH$_3$ | H | 4,6-dimethylpyrimidin-2-yl | 148–149 |
| (IV-12) | —CH$_2$COOC$_2$H$_5$ | H | 4,6-dimethylpyrimidin-2-yl | 98–99 |
| (IV-13) | —CH(CH$_3$)COOCH$_3$ | H | 4,6-dimethylpyrimidin-2-yl | 147–148 |
| (IV-14) | —CH$_2$—C$_6$H$_4$—CH$_3$ (p-tolylmethyl) | H | 4,6-dimethylpyrimidin-2-yl | 85–86 |
| (IV-15) | —CH$_2$—C$_6$H$_4$—F (2-fluorobenzyl) | H | 4,6-dimethylpyrimidin-2-yl | 114–116 |
| (IV-16) | cyclohexyl | H | 4,6-dimethylpyrimidin-2-yl | — |

TABLE 4-continued $$\begin{array}{c} O-R^1 \\ HN \\ \| \\ C-N \\ | \\ HN \end{array} \begin{array}{c} R_2 \\ R_3 \end{array}$$

| Example No. | R¹ | R² | R³ | Melting point (°C.) |
|---|---|---|---|---|
| (IV-17) | —CH₂—(cyclohexyl) | H | 4,6-dimethylpyrimidin-2-yl | |
| (IV-18) | —CH₂CON(CH₃)₂ | H | 4,6-dimethylpyrimidin-2-yl | |
| (IV-19) | —CH₂OCH₃ | H | 4,6-dimethylpyrimidin-2-yl | |
| (IV-20) | —CH₂SCH₃ | H | 4,6-dimethylpyrimidin-2-yl | |
| (IV-21) | —CH₂—C₆H₄—COOC₂H₅ (4-) | H | 4,6-dimethylpyrimidin-2-yl | 138 |
| (IV-22) | —CH₂CF₃ | H | 4,6-dimethylpyrimidin-2-yl | |
| (IV-23) | —CH₂—(2,6-dichlorophenyl) | H | 4,6-dimethylpyrimidin-2-yl | 140–145 |
| (IV-24) | —CH₂—C₆H₄—NO₂ (4-) | H | 4,6-dimethylpyrimidin-2-yl | 170–172 |

TABLE 4-continued $$\underset{HN}{\overset{O-R^1}{\underset{HN}{\vphantom{|}}}}C\underset{R_3}{\overset{R_2}{N}}$$

| Example No. | R¹ | R² | R³ | Melting point (°C.) |
|---|---|---|---|---|
| (IV-25) | —CH₃ | H | 2-methyl-4,6-dimethylpyrimidin-5-yl | 134–136 |
| (IV-26) | —C₂H₅ | H | 2-methyl-4,6-dimethylpyrimidin-5-yl | 88 |
| (IV-27) | —CH₂—C₆H₅ | H | 2-methyl-4,6-dimethylpyrimidin-5-yl | 102 |
| (IV-28) | —CH₃ | —CH₃ | 2-methyl-4,6-dimethylpyrimidin-5-yl | 95 |
| (IV-29) | —CH₃ | CH₃ | 2-methyl-4,6-dimethoxypyrimidin-5-yl | 135 |
| (IV-30) | —CH₃ | H | 2-methyl-4,6-dimethoxypyrimidin-5-yl | 122 |
| (IV-31) | —CH₃ | H | 2-methylpyrimidin-5-yl (4-CH₃) | 152 |
| (IV-32) | —CH₃ | H | 2-methyl-4-methoxy-6-methylpyrimidin-5-yl | 126 |

TABLE 4-continued $$\underset{HN}{\overset{O-R^1}{\underset{HN}{\vphantom{O}}}}C-N\underset{R_3}{\overset{R_2}{\vphantom{O}}}$$

| Example No. | R¹ | R² | R³ | Melting point (°C.) |
|---|---|---|---|---|
| (IV-33) | —CH₃ | H | 4-methoxy-6-methyl-2-(diethylamino)-1,3,5-triazinyl | 112 |
| (IV-34) | —CH₃ | H | 4-methylthio-6-methyl-2-(ethylamino)-1,3,5-triazinyl | 117 |
| (IV-35) | —CH₂CH₂CH₃ | H | 4,6-dimethylpyrimidin-2-yl | 54 |
| (IV-36) | —CH₂COOCH(CH₃)₂ | H | 4,6-dimethylpyrimidin-2-yl | 112 |
| (IV-37) | —C₂H₅ | H | 4-ethylpyrimidin-2-yl | — |
| (IV-38) | —CH₂C₆H₅ | H | 4-methylpyrimidin-2-yl | 150 |
| (IV-39) | —CH₂(2-Cl-C₆H₄) | H | 4-methylpyrimidin-2-yl | 140 |
| (IV-40) | —CH₃ | H | 4-methyl-6-methoxypyrimidin-2-yl | 126 |

TABLE 4-continued $$\underset{HN}{\overset{HN}{\underset{\|}{N}}}\overset{O-R^1}{\underset{R_3}{\overset{R_2}{N}}}$$

| Example No. | R¹ | R² | R³ | Melting point (°C.) |
|---|---|---|---|---|
| (IV-41) | —CH₃ | —CH₃ | 2-methyl-4-methoxy-6-methylpyrimidinyl | 135 |
| (IV-42) | —CH₃ | H | 2-methyl-4-(OCHF₂)-6-methylpyrimidinyl | |
| (IV-43) | —C₂H₅ | H | 2-methyl-4-OC₂H₅-6-methylpyrimidinyl | |
| (IV-44) | —CH₃ | H | 2,4,6-trimethylpyridinyl | 110 |
| (IV-45) | —CH₃ | H | 2-methyl-4,6-dimethoxypyrimidinyl | 122 |
| (IV-46) | —CHCH₂CH₃ ⎟ CH₃ | H | 2-methyl-4,6-dimethoxypyrimidinyl | 68 |
| (IV-47) | —CH₂CH(CH₃)₂ | H | 2-methyl-4,6-dimethoxypyrimidinyl | 76 |
| (IV-48) | —CH₃ | H | 2-methyl-4-ethylpyrimidinyl | 98 |

TABLE 4-continued $$\begin{array}{c} \text{O}-\text{R}^1 \\ \text{HN} \diagdown \diagup \text{R}_2 \\ \Vert \diagup \text{N} \diagdown \\ \text{HN} \quad \text{R}_3 \end{array}$$

| Example No. | $R^1$ | $R^2$ | $R^3$ | Melting point (°C.) |
|---|---|---|---|---|
| (IV-49) | —$C_2H_5$ | H | 4-methyl-2-pyrimidinyl | 95 |
| (IV-50) | —$CH_2$-(2-fluorophenyl) | H | 4-methyl-2-pyrimidinyl | 205 |
| (IV-51) | —$CH_2CH_2CH_2Cl$ | H | 4-methyl-2-pyrimidinyl | 102 |
| (IV-52) | —$CH_2COOC_2H_5$ | H | 4-methyl-2-pyrimidinyl | |
| (IV-53) | —$CH_2CH=CH_2$ | H | 4-methyl-2-pyrimidinyl | |
| (IV-54) | —$C_4H_9$—n | H | 4-methyl-2-pyrimidinyl | |
| (IV-55) | —$CH(CH_3)CH_2CH_3$ | H | 4-methyl-2-pyrimidinyl | |
| (IV-56) | —$CH_3$ | H | 4-methoxy-6-chloro-2-pyrimidinyl | 112 |
| (IV-57) | —$CH_3$ | H | 4,6-dimethyl-2-pyrimidinyl | 143 |

TABLE 4-continued

[Structure: HN-O-R¹, HN, N-R₂, N-R₃ guanidine core]

| Example No. | R¹ | R² | R³ | Melting point (°C.) |
|---|---|---|---|---|
| (IV-58) | —CH₂—C₆H₅ | H | pyrimidine with OCH₃, OCH₃ | 74 |
| (IV-59) | —CH₂—C₆H₅ | H | pyrimidine with CH₃, OCH₃ | $n_D^{20}$: 1.5645 |
| (IV-60) | —CH₂—C₆H₅ | H | pyrimidine with C₂H₅ | 112 |

Preparation of the starting materials of the formula (VI)

EXAMPLE (VI-1)

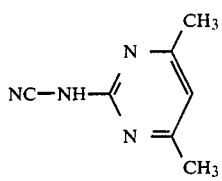

A mixture of 42 g (0.5 mol) of cyanoguanidine ("dicyanodiamide") and 50 g (0.5 mol) of pentane-2,4-dione ("acetylacetone") is heated to 120° C. for 15 hours. Thereafter, after the reaction mixture has been cooled, 500 ml of water are added and the solution is acidified with hydrochloric acid at 0° C. to 10° C. The product obtained in crystalline form in this procedure is isolated by being filtered off under suction. 51.8 g (70% of theory) of 2-cyanoamino-4,6-dimethyl-pyrimidine of melting point 205° C. are obtained.

EXAMPLE (VI-2)

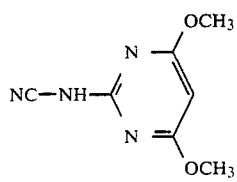

A solution, heated to 100° C., of 24 g (0.427 mol) of potassium hydroxide in 100 ml of water is added, at 100° C., to a stirred mixture of 9.2 g (0.043 mol) of 4,6-dimethoxypyrimidin-2-yl-thiourea and 70 ml of water. Stirring is continued for 2 minutes at 100° C., after which a solution, heated to 100° C., of 16.2 g (0.05 mol) of lead (II) acetate in 30 ml of water is added. The mixture is heated under reflux for a further 5 minutes and then cooled to 0° C. to 5° C., and 30 ml of glacial acetic acid are added to the aqueous solution. The product obtained in crystalline form in this procedure is isolated by being filtered off under suction.

6.3 g (81.5% of theory) of 2-cyanoamino-4,6-dimethoxy-pyrimidine of melting point 202° C. are obtained.

The compounds of the formula (VI) listed in Table 5 below can also be prepared by the processes described, by way of example, in Examples (VI-1), (VI-2) and (VI-3) above:

TABLE 5

[Structure: N≡C—N(R²)(R³)]

| Example No. | R² | R³ | Melting point (°C.) |
|---|---|---|---|
| (VI-3) | H | pyrimidine with CH₃ | 203 (decomposition) |
| (VI-4) | H | pyrimidine with OCH₃, CH₃ | 258 |

TABLE 5-continued $$N\equiv C-N\begin{array}{c}R^2\\R^3\end{array}$$

| Example No. | R² | R³ | Melting point (°C.) |
|---|---|---|---|
| (VI-5) | H | 4,6-pyrimidinyl with OCH₃ and N(C₂H₅)₂ | 114 |
| (VI-6) | H | 4,6-pyrimidinyl with SCH₃ and NHC₂H₅ | — |
| (VI-7) | H | 4,6-pyrimidinyl with OCH₃ and NHCH₃ | 210 |
| (VI-8) | H | 4,6-dimethylpyridinyl (CH₃, CH₃) | 221 |
| (VI-9) | H | pyrimidinyl with CH₃ and OC₂H₅ | — |
| (VI-10) | H | pyrimidinyl with CH₃ and SCH₃ | — |
| (VI-11) | H | pyrimidinyl with CH₃ and N(CH₃)₂ | — |
| (VI-12) | H | pyrimidinyl with CH₃ and OCHF₂ | 174 |
| (VI-13) | H | pyrimidinyl with CH₃ and COCH₃ | 174 |
| (VI-14) | H | pyrimidinyl with OH | 300 (decomposition) |
| (VI-15) | H | pyrimidinyl with C₂H₅ | 146 |
| (VI-16) | H | pyrimidinyl with CH₃ and COOC₂H₅ | 126 |
| (VI-17) | H | pyrimidinyl with CH₃ and CH₃ | 234 |
| (VI-18) | H | pyrimidinyl with OCH₃ and Cl | 200 |
| (VI-19) | H | pyrimidinyl with OC₂H₅ and Cl | — |
| (VI-20) | H | pyrimidinyl with CH₃ and Cl | — |
| (VI-21) | H | pyrimidinyl with OCH₃ and OCH₃ | — |

TABLE 5-continued $$N\equiv C-N\begin{matrix}R^2\\R^3\end{matrix}$$

| Example No. | $R^2$ | $R^3$ | Melting point (°C.) |
|---|---|---|---|
| (VI-22) | H | 4-methyl-pyridin-2-yl | 250 |
| (VI-23) | H | 4-chloro-6-dimethylamino-pyrimidin-2-yl | |
| (VI-24) | H | 4,6-diethoxy-pyrimidin-2-yl | |

2-(Alkyl-cyano-amino)-pyrimidines of the formula (VI) can be prepared, for example, as follows:

EXAMPLE (VI-25)

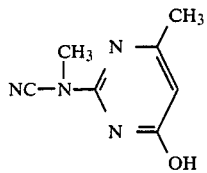

12.6 g (0.1 mol) of dimethyl sulphate are added dropwise to a solution of 15 g (0.1 mol) of 2-cyanoamino-4-hydroxy-6-methyl-pyrimidine and 4.1 g (0.1 mol) of sodium hydroxide in 60 ml of water, the reaction temperature increasing from 20° C. to 40° C. After stirring has been carried out for 2 hours at 20° C., the product obtained in crystalline form is isolated by being filtered off under suction.

11.1 g (68% of theory) of 2-(methyl-cyano-amino)-4-hydroxy-6-methyl-pyrimidine of melting point 290° C. are obtained.

The following compound is obtained analogously:

EXAMPLE (VI-26):

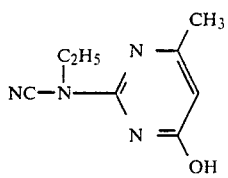

M.p.: 215° C. to 220° C.

EXAMPLE (VI-27):

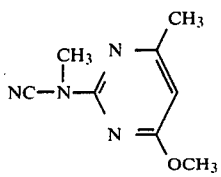

127.5 g (1 mol) of dimethyl sulphate are added dropwise to a solution of 75 g (0.5 mol) of 2-cyanoamino-4-hydroxy-6-methyl-pyrimidine and 44 g (1.1 mols) of sodium hydroxide in 750 ml of water, the reaction temperature increasing from 20° C. to 35° C. After stirring has been carried out for 12 hours at 20° C., the pH value is adjusted to between 9 and 10 by the addition of sodium hydroxide solution, and the product obtained in crystalline form is isolated by being filtered off under suction.

13 g (15% of theory) of 2-(methyl-cyano-amino)-4-methoxy-6-methyl-pyrimidine of melting point 123° C. are obtained.

The following compounds are obtained analogously.

EXAMPLE (VI-28):

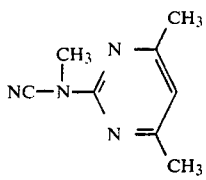

M.p.: 104° C.

EXAMPLE (VI-29):

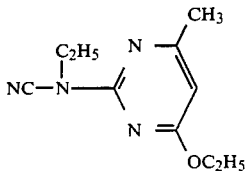

M.p.: 71° C.

Preparation of the starting materials of the formula (XII)

EXAMPLE

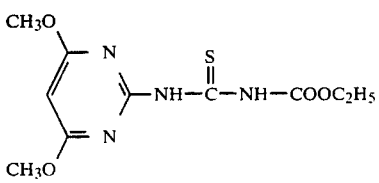

A mixture of 15.5 g (0.1 mol) of 2-amino-4,6-dimethoxypyrimidine, 13.1 g (0.1 mol) of ethoxycarbonyl isothiocyanate and 200 ml of acetonitrile is stirred for 2 hours at 60° C. Thereafter, the mixture is cooled to 10° C., and the product obtained in crystalline form is isolated by being filtered off under suction.

22.5 g (79% of theory) of 1-(ethoxycarbonyl)-3-(4,6-dimethoxy-pyrimidin-2-yl)-thiourea of melting point 194° C. (decomposition) are obtained.

The compounds of the formula (XII) listed in Table 6 below can be prepared by the process described, by way of example, in the example above:

TABLE 6

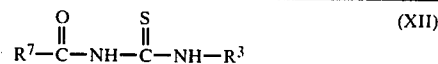

| Example No. | R⁷ | R³ | Melting point (°C.) |
|---|---|---|---|
| (XII-2) | 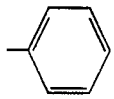 | 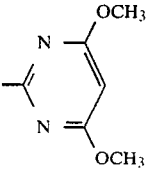 | 189 |
| (XII-3) | 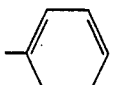 | 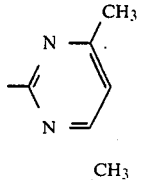 | 198-9 (decomposition) |
| (XII-4) | —OC₂H₅ |  | 217 |
| (XII-5) | 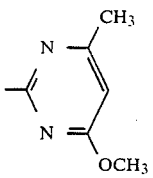 | 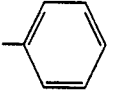 | 190 |
| (XII-6) | —OC₂H₅ | 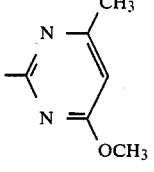 | 140 |
| (XII-7) |  | 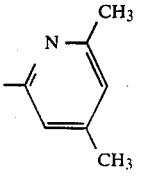 | 145 |
| (XII-8) | —OC₂H₅ | 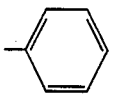 | 119 |
| (XII-9) | 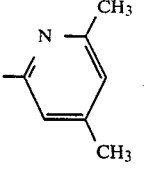 |  | 182 |
| (XII-10) | —OC₂H₅ | 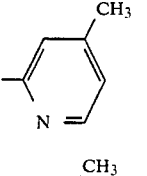 | 185 |
| (XII-11) | —OC₂H₅ | 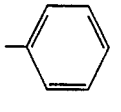 | 173 |
| (XII-12) | —OC₂H₅ | 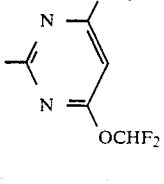 | 162 |
| (XII-13) | —OC₂H₅ |  | 169 |
| (XII-14) | 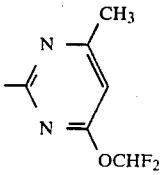 |  | 156 |
| (XII-15) | —OC₂H₅ | 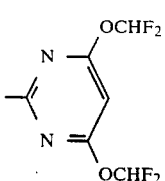 | 168 |
| (XII-16) |  | 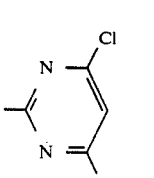 | 173 |
| (XII-17) |  | 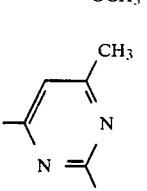 | 179 |

TABLE 6-continued $$R^7-\overset{O}{\underset{\|}{C}}-NH-\overset{S}{\underset{\|}{C}}-NH-R^3 \quad (XII)$$

| Example No. | $R^7$ | $R^3$ | Melting point (°C.) |
|---|---|---|---|
| (XII-18) | —OC$_2$H$_5$ | 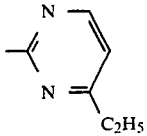 | |
| (XII-19) |  | 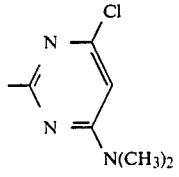 | 168 |
| (XII-20) | —OC$_2$H$_5$ | 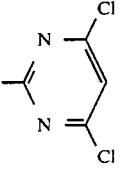 | 132–136 |
| (XII-21) | —OC$_2$H$_5$ | 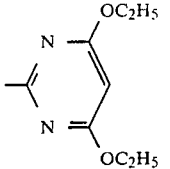 | |
| (XII-22) |  | 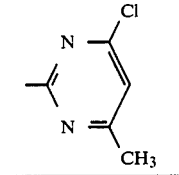 | 144 |

Preparation of the starting materials of the formula (XIII)

EXAMPLE (XIII-1)

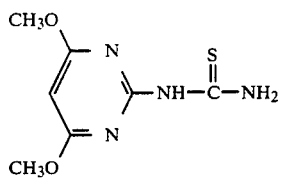

A mixture of 5.0 g (0.0175 mol) of 1-(ethoxycarbonyl)-3-(4,6-dimethoxy-pyrimidin-2-yl)-thiourea, 4.0 g (0.1 mol) of sodium hydroxide and 100 ml of water is stirred for 2 days at 20° C. Thereafter, dilute hydrochloric acid is added dropwise, while stirring, until the solution has been rendered acidic and evolution of CO$_2$ has ended. The product obtained in crystalline form is isolated by being filtered off under suction.

3.5 g (94% of theory) of 4,6-dimethoxypyrimidin-2-yl-thiourea of melting point 245°–8° C. (decomposition) are obtained.

The compounds of the formula (XIII) listed in Table 7 below can be prepared by the process described, by way of example, in the example above:

TABLE $$R^3-NH-\overset{S}{\underset{\|}{C}}-NH_2 \quad (XIII)$$

| Example No. | $R^3$ | Melting point (°C.) |
|---|---|---|
| (XIII-2) | 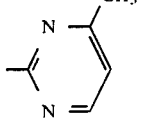 | 264–265 (decomposition) |
| (XIII-3) | 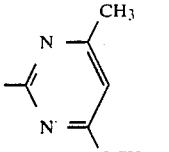 | 205–207 (decomposition) |
| (XIII-4) | 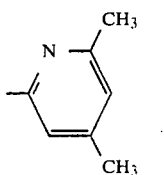 | 259–260 (decomposition) |
| (XIII-5) | 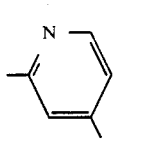 | 214–215 |
| (XIII-6) | 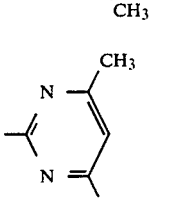 | 192–194 |
| (XIII-7) | 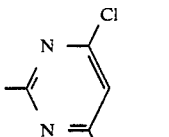 | 225–227 (decomposition) |
| (XIII-8) | 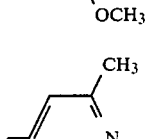 | 248 |
| (XIII-9) | 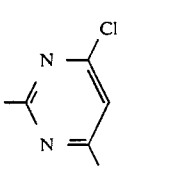 | |

TABLE-continued $$R^3-NH-\overset{\overset{S}{\|}}{C}-NH_2 \quad (XIII)$$

| Example No. | $R^3$ | Melting point (°C.) |
|---|---|---|
| (XIII-10) | 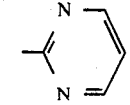 | 263 |
| (XIII-11) | 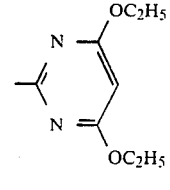 | |
| (XIII-12) | 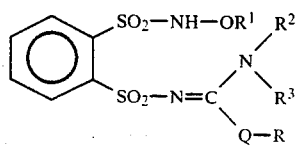 | |

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the active compounds according to the preparation Examples (1) and (4) exhibit a better herbicidal activity against mono- and dicotyledon weeds as the compound (A).

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the active compounds according to the preparation Examples (1) and (4) exhibit a better herbicidal activity against mono- and dicotyledon weeds as the compound (A).

It is understood that the specification and examples are illustrative but not limitative of the present invention and that other embodiments within the spirit and scope of the invention will suggest themselves to those skilled in the art.

We claim:

1. A 1-2-oxyaminosulphonylphenylsulphonyl)-3-heteroaryliso(thio)-urea of the formula

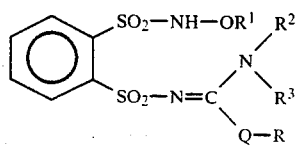

in which

R is $C_1-C_{12}$-alkyl (which is optionally substituted by fluorine, chlorine, cyano, $C_1-C_4$-alkoxy, $C_1-C_4$-alkylthio, $C_1-C_4$-alkylsulphinyl, $C_1-C_4$-alkylsulphonyl, $C_1-C_4$-alkyl-carbonyl, $C_1-C_4$-alkoxy-carbonyl, $C_1-C_4$-alkylamino-carbonyl or di-($C_1-C_4$-alkyl)-amino-carbonyl): $C_3-C_6$-alkenyl, $C_3-C_6$-alkinyl, $C_3-C_6$-cycloalkyl, $C_3-C_6$-cycloalkyl-$C_1$- or $C_2$-alkyl; phenyl-$C_1$- or $C_2$-alkyl (which is optionally substituted by fluorine, chlorine, nitro, cyano, $C_1-C_4$-alkyl, $C_1-C_4$-alkoxy or $C_1-C_4$-alkoxy-carbonyl); or phenyl (which is optionally substituted by one or more radicals from halogen, cyano, nitro, hydroxyl, carboxyl, $C_1-C_6$-alkyl, $C_3-C_6$-cycloalkyl, $C_1-C_4$-alkoxy, $C_1-C_4$-alkylthio, amino, $C_1-C_4$-alkyl-amino or di-($C_1-C_4$-alkyl)-amino, $C_1-C_4$-alkylcarbonyl-amino, $C_1-C_4$-alkoxycarbonyl-amino, (di)-$C_1-C_4$-alkylamino-carbonyl-amino, formyl, $C_1-C_4$-alkyl-carbonyl, benzoyl, $C_1-C_4$-alkoxy-carbonyl, phenoxycarbonyl, benzyloxycarbonyl, phenyl, phenoxy, phenylthio, phenylsulphonyl phenylamino, phenylazo, pyridyloxy, pyrimidyloxy, $C_1-C_4$-alkyl-carbonyloxy, $C_1-C_4$-alkoxy-carbonyl-oxy, $C_1-C_4$-alkyl-amino-carbonyl-oxy and di-($C_1-C_4$-alkyl)-amino-carbonyl-oxy;

$R^1$ is $C_1-C_{12}$-alkyl (which is optionally substituted by fluorine, chlorine, cyano, $C_1-C_4$-alkoxy, $C_1-C_4$-alkylthio, $C_1-C_4$-alkylsulphinyl, $C_1-C_4$-alkylsulphonyl, $C_1-C_4$-alkyl-carbonyl, $C_1-C_4$-alkoxy-carbonyl, $C_1-C_4$-alkylamino-carbonyl or di-($C_1-C_4$-alkyl)-amino-carbonyl); $C_3-C_6$-, alkenyl, $C_3-C_6$-alkinyl, $C_3-C_6$-cycloalkyl, $C_3-C_6$-cycloalkyl-$C_1$- or $C_2$-alkyl; phenyl- $C_1$- or $C_2$-alkyl (which is optionally substituted by fluorine, chlorine, nitro, cyano, $C_1-C_4$-alkyl, $C_1-C_4$-alkoxy or $C_1-C_4$-alkoxy-carbonyl); or phenyl (which is optionally substituted by fluorine, chlorine, nitro, cyano, $C_1-C_4$-alkyl, trifluoromethyl, $C_1-C_4$-alkoxy, $C_1$- or $C_2$-fluoroalkoxy, $C_1$-$C_4$-alkylthio, trifluoromethylthio or $C_1$-$C_4$-alkoxy-carbonyl), $R^2$ is hydrogen; $C_1$-$C_4$-alkyl (which is optionally substituted by fluorine, chlorine, cyano, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_4$-alkoxy-carbonyl, $C_1$-$C_4$-alkylamino-carbonyl or di-($C_1$-$C_4$-alkyl)-amino-carbonyl) $C_3$-$C_6$-alkenyl; $C_3$-$C_6$-alkinyl; or phenyl-$C_1$- or $C_2$-alkyl (which is optionally substituted by fluorine, chlorine, nitro, cyano, $C_1$-$C_4$-alkyl, $C_1$-$C_4$-alkoxy or $C_1$-$C_4$-alkoxy-carbonyl), $R^3$ is

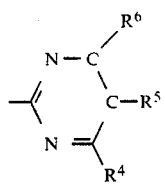

$R^4$ is hydrogen, fluorine, chlorine, bromine, hydroxyl, $C_1$-$C_4$-alkyl (which is optionally substituted by fluorine and/or chlorine), $C_1$-$C_4$-alkoxy (which is optionally substituted by fluorine and/or chlorine), $C_1$-$C_4$-alkylthio (which is optionally substituted by fluorine and/or chlorine), amino, $C_1$-$C_4$-alkylamino or di-($C_1$-$C_4$-alkyl)-amino, $R^5$ is hydrogen, fluorine, chlorine, bromine or $C_1$-$C_4$-alkyl, $R^6$ is hydrogen, fluorine, chlorine, bromine, hydroxyl, $C_1$-$C_4$-alkyl (which is optionally substituted by fluorine and/or chlorine), $C_1$-$C_4$-alkoxy (which is optionally substituted by fluorine and/or chlorine), $C_1$-$C_4$-alkylthio (which is optionally substituted by fluorine and/or chlorine), amino, $C_1$-$C_4$-alkylamino or di-($C_1$-$C_4$-alkyl)-amino, and Q is oxygen or sulfur, or a strong acid-adduct thereof.

2. A compound or adduct according to claim 1, in which

R is $C_1$-$C_8$-alkyl (which is optionally substituted by fluorine or chlorine), $C_3$- or $C_4$-alkenyl, $C_1$- or $C_2$-alkoxy-carbonylmethyl, phenylethyl or benzyl (which is optionally substituted by fluorine, chlorine, nitro, cyano, methyl, methoxy or methoxycarbonyl), or phenyl (which is optionally substituted by one or two radicals from the series comprising fluorine, chlorine, bromine, iodine, cyano, nitro, hydroxyl, carboxyl, $C_1$-$C_3$-alkoxy-carbonyl, $C_1$-$C_4$-alkyl, cyclohexyl, $C_1$-$C_3$-alkoxy, $C_1$-$C_3$-alkylthio, dimethylamino, amino, acetylamino, formyl, acetyl, benzoyl, phenyl, phenoxy, phenylamino, phenylazo and pyridloxy);

$R^1$ is $C_1$-$C_8$-alkyl (which is optionally substituted by fluorine or chlorine), $C_3$- or $C_4$-alkenyl, $C_1$- or $C_2$-alkoxy-carbonylmethyl, phenyl-ethyl or benzyl (which is optionally substituted by fluorine, chlorine, nitro, cyano, methyl, methoxy or methoxycarbonyl), $R^2$ is hydrogen, $R^4$ is chlorine, methyl, methoxy or ethoxy, $R^5$ is hydrogen, and $R^6$ is hydrogen, chlorine, methyl, methoxy, ethoxy, methylthio, ethylhio, dimethylamino or diethylamino.

3. A compound according to claim 1 wherein such compound is N'-(4,6-dimethylpyrimidin-2-yl)-N''-(2-methoxyaminosulphonylphenylsulphonyl)-S-methyl-isothiourea of the formula

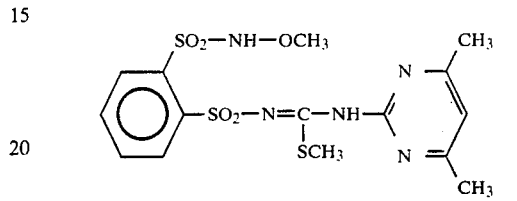

or a strong acid-adduct thereof.

4. A compound according to claim 1, wherein such compound is N'-(4,6-dimethylpyrimidin-2-yl)-N''-(2-methoxyaminosulphonylphenylsulphonyl)-S-phenyl-isothiourea of the formula

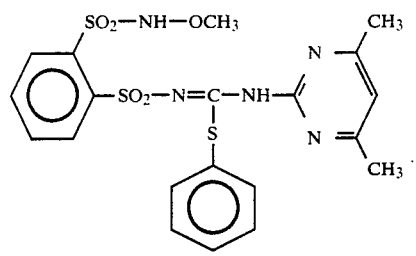

or a strong acid-adduct thereof.

5. A herbicidal composition comprising a herbicidally effective amount of a compound or adduct according to claim 1 in admixture with a diluent.

6. A method of combating unwanted vegetation which comprises applying to such vegetation or to a locus from which it is desired to exclude such vegetation a herbicidally effective amount of a compound or adduct according to claim 1.

7. The method according to claim 6, wherein such compound is N'-(4,6-dimethylpyrimidin-2-yl)-N''-(2-methosyaminosulphonylphenylsulphonyl)-S-methyl-isothiorurea.

8. The method according to claim 6, wherein such compound is N'-(4,6-dimethylpyrimidin-2-yl)-N''-(2-methoxyaminosulphonylphenylsulphonyl)-S-phenyl-isothiourea.

* * * * *